(12) United States Patent
King

(10) Patent No.: US 9,642,974 B2
(45) Date of Patent: May 9, 2017

(54) METHOD AND APPARATUS FOR WARMING INTRAVENOUS FLUIDS

(75) Inventor: David R. King, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 827 days.

(21) Appl. No.: 13/820,779

(22) PCT Filed: Sep. 12, 2011

(86) PCT No.: PCT/US2011/051245
§ 371 (c)(1),
(2), (4) Date: May 14, 2013

(87) PCT Pub. No.: WO2012/037037
PCT Pub. Date: Mar. 22, 2012

(65) Prior Publication Data
US 2013/0226087 A1    Aug. 29, 2013

Related U.S. Application Data

(60) Provisional application No. 61/383,060, filed on Sep. 15, 2010.

(51) Int. Cl.
*A61M 5/44*         (2006.01)
*F24J 1/00*         (2006.01)
*A61M 5/142*        (2006.01)

(52) U.S. Cl.
CPC ..... *A61M 5/44* (2013.01); *A61M 2005/14272* (2013.01); *A61M 2205/3368* (2013.01); *A61M 2205/364* (2013.01); *F24J 1/00* (2013.01)

(58) Field of Classification Search
CPC ............ A61M 5/44; A61M 2205/3368; A61M 2205/364; A61M 2005/142752; F24J 1/00
(Continued)

(56) References Cited

U.S. PATENT DOCUMENTS 1,043,120 A * 11/1912 Lombard ............. A62C 13/003
                                                 126/263.05
1,493,450 A *  5/1924 Richardson ................... 392/480
(Continued)

FOREIGN PATENT DOCUMENTS

JP          09075387 A  *  3/1997  ............... A61F 7/08
JP      2002119586 A  *  4/2002
(Continued)

OTHER PUBLICATIONS

Smith, et al., Principles of Fluid and Blood Warming in Trauma, International TraumaCare (ITACCS), 2008, 18 (1):71-79.
(Continued)

*Primary Examiner* — Gregory Huson
*Assistant Examiner* — Daniel E Namay
(74) *Attorney, Agent, or Firm* — Quarles & Brady LLP

(57) ABSTRACT

A system and method for warming a fluid for intravenous administration is presented. The system includes an enclosure, a frangible bladder disposed at least partially within the enclosure, and a first reactant of an exothermic reaction disposed within the frangible bladder. The apparatus includes a second reactant of the exothermic reaction disposed within the enclosure and external to the frangible bladder, and a channel at least partially enclosed by the enclosure. The frangible bladder is configured to be ruptured to mix at least a portion of the first reactant and the second reactant to initiate the exothermic reaction, thereby warming at least a portion of the channel.

20 Claims, 3 Drawing Sheets

(58) Field of Classification Search
USPC .......................................... 126/263.05, 263.01
IPC ....................................... A61M 5/44; F24J 1/00
See application file for complete search history.

(56) References Cited

U.S. PATENT DOCUMENTS

| | | | | |
|---|---|---|---|---|
| 1,613,120 | A | * | 1/1927 | O'Neal et al. .................. 44/252 |
| 3,550,578 | A | * | 12/1970 | Foss et al. ..................... 156/296 |
| 3,950,158 | A | * | 4/1976 | Gossett ............................... 62/4 |
| 3,963,892 | A | * | 6/1976 | Camph et al. ................ 219/687 |
| 4,057,047 | A | * | 11/1977 | Gossett .................... 126/263.07 |
| 4,334,519 | A | * | 6/1982 | Cieslak et al. ................ 126/204 |
| 4,662,352 | A | * | 5/1987 | Aviles, Jr. ......... A61M 16/1075 |
| | | | | 126/204 |
| 5,101,804 | A | | 4/1992 | Cohn |
| 5,263,929 | A | | 11/1993 | Falcone et al. |
| 5,456,704 | A | * | 10/1995 | Kilcullen ..................... 607/111 |
| 6,142,974 | A | | 11/2000 | Kistner et al. |
| 7,158,719 | B2 | | 1/2007 | Cassidy |
| 2002/0174863 | A1 | * | 11/2002 | Saric et al. ............. 126/263.05 |
| 2003/0114795 | A1 | | 6/2003 | Faries et al. |
| 2003/0163087 | A1 | * | 8/2003 | Noice .................... A61M 5/44 |
| | | | | 604/113 |
| 2005/0224388 | A1 | * | 10/2005 | Saric et al. .................. 206/554 |
| 2005/0224389 | A1 | * | 10/2005 | Azzolini et al. .............. 206/570 |
| 2007/0088263 | A1 | | 4/2007 | Noice et al. |
| 2007/0105010 | A1 | | 5/2007 | Cassidy |
| 2007/0142773 | A1 | * | 6/2007 | Rosiello et al. ............. 604/113 |
| 2008/0257333 | A1 | * | 10/2008 | Dodo et al. ............. 126/263.09 |
| 2009/0234287 | A1 | * | 9/2009 | Temple ......................... 604/113 |
| 2010/0083965 | A1 | * | 4/2010 | Virr et al. ................. 128/203.26 |
| 2010/0147282 | A1 | * | 6/2010 | Urume .................... A47J 36/28 |
| | | | | 126/263.05 |
| 2010/0241089 | A1 | * | 9/2010 | Uchiyama ..................... 604/291 |
| 2010/0280454 | A1 | * | 11/2010 | Rosiello ........................ 604/114 |

FOREIGN PATENT DOCUMENTS

| | | | | |
|---|---|---|---|---|
| SG | WO 2010134893 | A1 | * 11/2010 | ............... A61J 1/10 |
| WO | WO 0048646 | A2 | * 8/2000 | .............. A61M 5/44 |

OTHER PUBLICATIONS

Taub, et al., Mechanism of Dihydrogen Formation in the Magnesium-Water Reaction, Journal of Physical Chemistry A, 2002, 106(35):8070-8078.

International Search Report and Written Opinion as mailed on Apr. 26, 2012 for International Application No. PCT/US2011/051245.

* cited by examiner

METHOD AND APPARATUS FOR WARMING INTRAVENOUS FLUIDS

CROSS-REFERENCE TO RELATED APPLICATIONS

This application represents the U.S. National Stage of International Application No. PCT/US2011/051245, filed Sep. 12, 2011 which is based on, claims the benefit of, and incorporates by reference U.S. Provisional Application Ser. No. 61/383,060, filed Sep. 15, 2010, and entitled "METHOD AND APPARATUS FOR WARMING INTRAVENOUS FLUIDS."

FIELD OF THE INVENTION

The present invention relates to a method and apparatus for fluid warming and, specifically, a method and apparatus for providing a portable and self-heating warmer configured to heat fluids using a controlled exothermic chemical reaction.

BACKGROUND OF THE INVENTION

Emergency medical treatment for hemorrhage control often calls for the administration of direct pressure and intravenous fluid resuscitation. This can be particularly true in the case of combat casualty care in a far forward military or hostile environment where resources commonly found in hospital emergency rooms are unavailable.

Although intravenous fluid resuscitation can often provide relatively prompt therapeutic benefit to a patient, a recent statement by the Department of Defense Prehospital Combat Casualty Care Fluid Resuscitation Consortium indicated that cold or room temperature fluid may not provide any benefit whatsoever. In fact, in some cases, the delivery of cold or room temperature fluid may even be harmful to the patient. In general, the fluid must be warmed before administration in order to generate the desired therapeutic effect.

Although some technologies exist for portable heating of intravenous fluids, they are generally battery operated, making them prone to short rucksack shelf life and prohibitively heavy.

SUMMARY OF THE INVENTION

The present invention relates to a method and apparatus for fluid warming and, specifically, a method and apparatus for providing a portable and self-heating fluid warmer configured to heat fluids using a controlled exothermic reaction.

In one implementation, the present invention is an apparatus for warming a fluid for intravenous administration. The apparatus comprises an enclosure, a frangible bladder disposed at least partially within the enclosure, and a first reactant of an exothermic reaction disposed within the frangible bladder. The apparatus includes a second reactant of the exothermic reaction disposed within the enclosure and external to the frangible bladder, and a channel at least partially enclosed by the enclosure. The frangible bladder is configured to be ruptured to mix at least a portion of the first reactant and the second reactant to initiate the exothermic reaction, thereby warming at least a portion of the channel. The apparatus includes an input configured to receive a fluid from a fluid source and deliver the fluid to the channel to be exposed to the at least a portion of the channel warmed by the exothermic reaction, and an output configured to receive the fluid from the channel after being exposed to the at least a portion of the channel warmed by the exothermic reaction and to be coupled to an intravenous administration system to deliver the fluid for intravenous administration.

In another implementation, the present invention is an apparatus for warming a fluid. The apparatus includes a housing having an opening, and a reactor sized to fit within the opening of the housing. The reactor includes a frangible bladder configured to contain a first reactant of an exothermic reaction, and a channel at least partially enclosed by the reactor. The frangible bladder is configured to be ruptured to initiate the exothermic reaction, thereby warming at least a portion of the channel.

In another implementation, the present invention is a method of warming a fluid. The method includes providing an enclosure including a frangible bladder disposed at least partially within the enclosure, a reactant of an exothermic reaction disposed within the frangible bladder, and a channel at least partially enclosed by the enclosure. The method includes rupturing the frangible bladder to initiate the exothermic reaction, and, after rupturing the frangible bladder, flowing a fluid through the channel to cause the fluid to be warmed by the exothermic reaction.

In another implementation, the present invention includes an apparatus for warming a fluid. The apparatus includes an enclosure, a frangible bladder disposed at least partially within the enclosure, and a first reactant of an exothermic reaction disposed within the frangible bladder. The apparatus includes a second reactant of the exothermic reaction disposed within the enclosure and external to the frangible bladder, and a channel at least partially enclosed by the enclosure. The frangible bladder is configured to be ruptured to mix at least a portion of the first reactant and the second reactant to initiate the exothermic reaction, thereby warming at least a portion of the channel.

The foregoing and other aspects and advantages of the invention will appear from the following description. In the description, reference is made to the accompanying drawings which form a part hereof, and in which there is shown by way of illustration at least one embodiment of the invention. Such embodiment does not necessarily represent the full scope of the invention, however, and reference is made therefore to the claims and herein for interpreting the scope of the invention.

DETAILED DESCRIPTION

The present invention relates to a method and apparatus for fluid warming and, specifically, a method and apparatus for providing a portable and self-heating fluid warmer configured to heat fluids using a controlled exothermic reaction.

Figure 1:
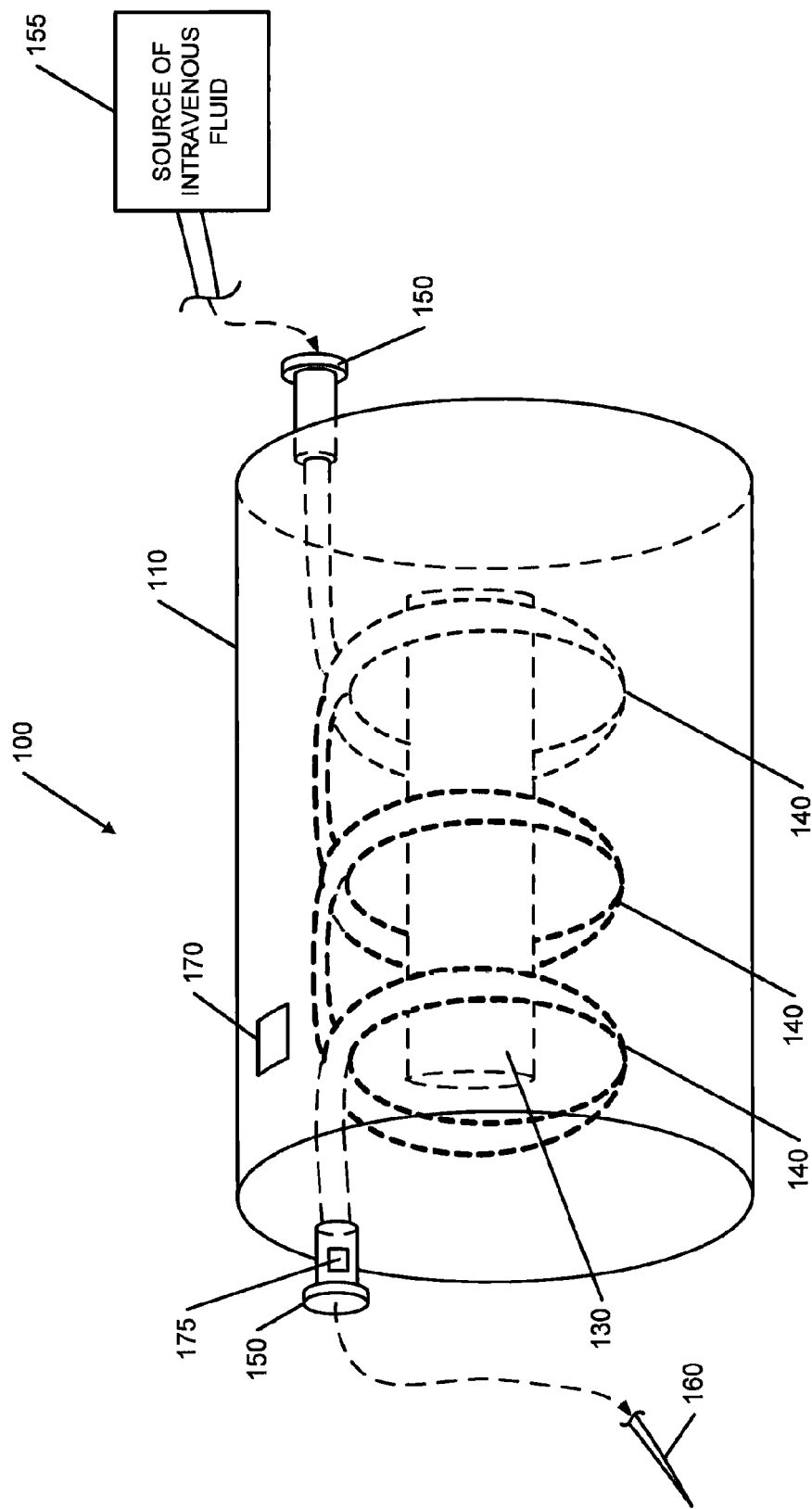
FIG. 1 is an illustration of a fluid warming apparatus including an enclosure and a frangible bladder.

FIG. 1 is an illustration of a fluid warming apparatus 100, which may be used for warming intravenous fluids for delivery to a patient. The warming apparatus 100 includes an enclosure 110, which can optionally be insulated along at least a portion of an outer surface thereof to reduce transfer of heat between an interior of the enclosure 110 and the local external environment (e.g., the surrounding air if used in an open space).

In one exemplary embodiment, the enclosure 110 can be flexible, and the apparatus 100 further includes at least one frangible bladder arrangement 130 provided within the enclosure 110. At least one reactant substance capable of generating or catalyzing an exothermic reaction can be provided within the bladder arrangement 130. At least one further reactant can be provided within the enclosure 110 but external to the bladder arrangement 130, such that the bladder arrangement 130 prevents or inhibits mixing of the reactants while the bladder arrangement 130 remains intact. The reactants can include certain substances (for example, magnesium, or a combination of cellulose, iron, water, activated carbon, vermiculite, and salt, as described below) that react chemically with each other to generate heat, a catalyst or other substance that can promote or facilitate an exothermic chemical or phase-change reaction, or the like.

It should be noted that the system illustrated in FIG. 1 includes two frangible bladders or compartments. The first frangible bladder or compartment comprises element 130. The second frangible bladder or compartment comprises the remaining volume within enclosure 110 that excludes bladder 130. Accordingly, "bladder" may be defined positively (for example, as a volume contained within a particular component of the system), or negatively (for example, by the remaining volume within an enclosure that excludes other bladders or compartments).

The internal bladder arrangement 130 can then be ruptured, punctured, or otherwise breached, for example, by squeezing or bending the warming apparatus 100, to allow a mixture of the bladder arrangement 130's contents with the reactant(s) contained within the enclosure 110 and outside of the bladder arrangement 130, thereby initiating the exothermic reaction. This configuration facilitates separation of certain reactants of the exothermic reaction, and prevents initiation and/or propagation of the exothermic reaction until a warming effect is desired.

In some implementations, the reactants contained within warming apparatus 100 include chemicals (for example, similar to those found in a diphenyl oxalate chemiluminescence stick) that are selected to generate light upon mixing of the reactants. In that case, the presence of light can be used as in indicator to provide a user with notice that the warming reaction is taking place and that the fluid flowing through the warming apparatus 100 is being warmed. In that case, the light-generating reactants may be disposed within a separate bladder, such as a plastic tube, that is configured to break or rupture when the warming apparatus 100 is used. Alternatively, the light-emitting reactants may be disposed within the same frangible bladders or compartments as the heat-generating reactants, if possible.

In some implementations, the exemplary warming apparatus 100 is provided in a rigid, protective enclosure to prevent accidental rupturing of the bladder arrangement 130 during storage or transportation.

Additional chemicals or substances may be provided within the bladder arrangement 130 and/or within the enclosure 110 and outside of the bladder arrangement 130. The additional substances can be selected, for example, to catalyze and/or control a rate of the exothermic reaction, to facilitate conduction of heat generated by the exothermic reaction, to cushion or protect the contents of the enclosure 110, and the like. These additional substances can include, for example, cellulose, activated carbon, vermiculite, salt, a gelation agent, an emulsifier, and the like. The additional substances selected for a particular application can be based on the particular exothermic reaction to be initiated within the enclosure 110.

The warming apparatus 100 includes a hollow channel 140 provided within the enclosure 110. The hollow channel 140 can be formed from or coated with a biocompatible and/or inert material, and may have a high thermal conductivity to efficiently transfer heat from the outside of the channel 140 to a fluid, or a tubing containing a fluid contained therein. The channel 140 can be flexible to reduce the risk of fracture or breakage of the channel 140 within the enclosure 110, for example, during storage or transportation or initiation of the warming reaction. In other implementations, however, the channel 140 may include an open volume within enclosure 110 configured to receive a fluid. In that case, colder fluid would enter the volume at a bottom portion of the volume. As the fluid is heated, warmer fluid moves to the top of the volume where it eventually exits the volume through an appropriate outlet.

The ends of the hollow channel 140 can protrude from an outer surface of the enclosure 110 as shown in FIG. 1, or alternatively one or both ends can be substantially flush with the surface of the enclosure 110. A connecting arrangement or connector 150 can be provided at each end of the channel 140, for example, where the channel 140 joins the surface of the enclosure 110 or protrudes therefrom. The connecting arrangement can include, for example, a Luer-Lock or any other fastener configured to couple or affix a tube or other conduit or lumen to the channel 140.

Alternatively, the channel 140 may be sized so that a length of intravenous tubing (or the like) can be threaded through channel 140. In that case, heat is communicated from channel 140 into the body of the tubing, before being transmitted into the liquid flowing through the tubing.

The length of channel 140 is selected to allow fluid flowing there-through to be heated to a particular temperature, or range or temperatures. Given a particular fluid flow rate, or range of flow rates, it is possible to determine a time duration for which fluid will be present within channel 140. Also, based upon the components of the exothermic reaction occurring within warming apparatus 100, it is possible to determine how much heat is generated by the reaction and transmitted into channel 140. Then, based upon an anticipated ambient or room temperature, it is possible to select a particular length for channel 140 that will cause fluid flowing through channel 140 to be heated from ambient or room temperature, to a desired output temperature or range of temperatures.

A source of intravenous fluid 155 or the like can be affixed to a first end of the channel 140 using the connecting arrangement 150. The second end of the channel 140 can be affixed to a tube leading to an intravenous needle 160 inserted in the patient, or to some other fluid delivery arrangement, using the connecting arrangement 150. The exothermic reaction can be initiated within the enclosure 110, for example, by rupturing the bladder arrangement 130, and intravenous fluid can be allowed to flow through the channel 140. Heat will be generated by the exothermic reaction and transferred by conductance to the walls of the channel 140, and further to the fluid passing there-through to heat the fluid. In this manner, the fluid can be controllably heated as it passes through the channel 140 before exiting and being delivered to the patient, e.g., through a needle.

In a further embodiment, one or more thermal indicators 170, 175 can be provided on the warming device 100. For example, such thermal indicators 170, 175 can be color-changing films that indicate a particular color when the local temperature is at a desired value or within a desired temperature range. Other types of thermal indicators 170, 175 may also be used. Such thermal indicators 170, 175 can be low-cost, disposable, and/or battery-less. If the thermal indicators 170,175 do not indicate an elevated temperature, the exothermic reaction reactants may be depleted and the warming device 100 may need to be replaced to heat additional fluid being administered.

Alternatively or additionally, a thermal indicator 175 can be provided on a portion of the channel 140 at or proximal to where the channel 140 exits the enclosure 110, also shown in FIG. 1. The thermal indicator 175 can be used to indicate whether the fluid exiting the warming device 100 is at a desired temperature or within a desired temperature range. Such thermal indicator 175 can provide a signal to indicate whether the fluid is too warm, too cool, or at a desired temperature.

The reactants and other substances provided in the warming apparatus 100 (for example, catalysts, reaction rate-limiting substances, and the like) can be selected to generate a slow reaction when mixed as described herein. Such a slow or controlled reaction may provide warming of fluids for a long period of time, for example, on the order of an hour or more. The reaction preferably can occur at a substantially constant reaction temperature that does not vary significantly as the reaction progresses. The reaction temperature, in one implementation, is at or close to the desired temperature of the fluids (for example, the desired temperature of fluids to be delivered to a patient—within a few degrees of normal body temperature). Such a reaction temperature can facilitate more reliable and safe heating of the fluid passing through the warming apparatus 100 by avoiding potential overheating through exposure of the fluid to temperatures much higher than required. In other implementations, though, the reaction temperature may be significantly higher than required, allowing for rapid heating of fluids within the heating device to a desired temperature (even if the desired temperature is less than that of the reaction).

Further embodiments of the exemplary warming apparatus 100 shown in FIG. 1 can be provided to accommodate variations in the environment, such as hot or cold ambient temperatures. For example, the length of the channel 140 within the enclosure 110 can be longer if the warming apparatus 100 is used in a cold environment, to facilitate sufficient warming of colder fluids introduced into the channel 140. The warming apparatus 100 can be provided with a shorter channel 140 if it is to be used in warmer environments, where it is desirable to transmit less heat into the fluid before.

In some cases, to treat patients suffering from heat-induced disorders, such as heat stroke, the heating element of the device may be replaced by an element configured to cool (for example, using an endothermic chemical reaction) the intravenous fluids flowing there-through before delivery to the patient. In certain embodiments, a plurality of channels 140 can be provided within the enclosure 110, where the different channels 140 each has a different length selected to facilitate different degrees of heating of fluid passing there-through. Such channels 140 can be selectable using one or more valve arrangements, which can be accessible externally to the enclosure if provided. A relatively long channel 140 can be used in a range of environments if the exothermic reaction temperature is very close to the desired temperature, such that the residence time of the fluid within the channel 140 is sufficient to bring the fluid to substantially the same temperature as that of the reaction mixture contained within the enclosure 100.

In one embodiment, the warming apparatus 100 can be a single-use, disposable device. Low-cost components may be used, and the apparatus 100 may be discarded after the reactants have been used up in the exothermic reaction or a sufficient amount of fluid has been warmed.

The warming apparatus 100 can be lightweight and easily transportable, such that it can be carried in the deployed environment and benefit austere casualty situations where fluid resuscitation is indicated. It can be placed proximal to a patient, unlike most standard fluid warming systems. Instead of heating an entire bag of intravenous fluid (where fluid cooling and heat loss can occur along the intravenous tubing on the way to the patient), the warming apparatus 100 can be placed at the distal end of the intravenous tubing, proximal to where the fluid enters the patient, thus eliminating the need to pre-warm large volumes of high specific heat fluid. This approach is consistent with the principle of hypotensive resuscitation and facilitates conservative use of intravenous fluids by warming only the fluid volume that will actually be infused into the patient, instead of warming the entire reservoir.

Figure 2:
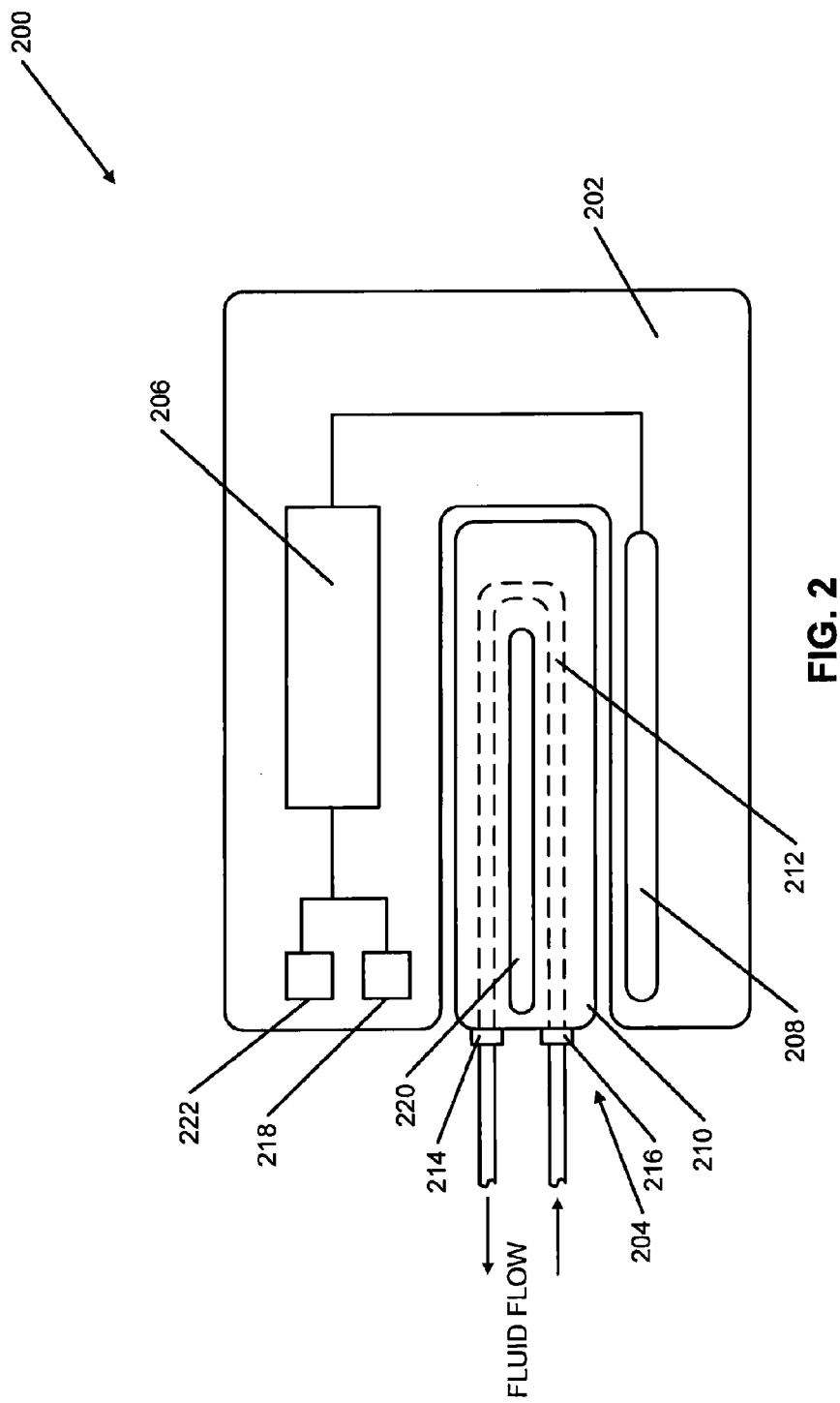
FIG. 2 is a side view of an alternative implementation of the present fluid warming system incorporating a chuck or housing for containing a warming reactor.

Referring now to FIG. 2, a side view of another implementation of the present fluid warming system is provided that incorporates a chuck or housing for containing a warming reactor. Reactants contained within the reactor mix and undergo an exothermic chemical reaction. The heat generated by that reaction is used to warm fluids flowing through the warming system 200.

The warming system 200 includes the chuck or housing 202 for housing a number of components of warming system 200 and forming a receptacle for the heating element or reactor of the device. The components can be disposed within the housing 202, or inserted into the opening 204 of the housing 202, as shown in FIG. 2.

The housing 202 may include various electronic components such as a controller 206 for controlling the operation of the warming system 200. For example, the controller 206 may incorporate or be in communication with temperature sensors and other controllers (for example, thermocouples, resistance temperature detectors (RTDs), or liquid crystals) to monitor and control the temperature of fluids being delivered by the warming system 200.

The controller 206 is in communication with flow rate controllers 218 for controlling a fluid flow rate of, for example, intravenous fluids being delivered to a patient through the system. The temperature of the fluids being delivered can be controlled by controlling the fluid flow rate. For example, if the fluid temperature is too high, the controller 206 can instruct the fluid flow controller 218 to increase the fluid flow rate, thereby decreasing an amount of heat transmitted into the fluid before delivery. Similarly, if the temperature is too low, fluid flow rate can be decreased. In one implementation, to control fluid flow, fluid flow controller 218 is in communication with one or more of couplings 214 and 216 that include actuators for controlling fluid flow there-through. The fluid flow controller 218 may be in direct wired communication with one or more of the couplings 214 and 216 or may communicate wirelessly. Alternatively, the controller 206 can, upon detecting that the fluid is too hot or cold, use a user interface 222 to instruct a user of the system 200 to modify a fluid flow through the system, for example by modifying the operation of an infusion pump connected to the system. Alternatively, a doctor using the system to administer intravenous fluid may squeeze or otherwise manipulate a connected intravenous fluid bag to increase fluid flow through the system. Exemplary user interfaces 222 include LCD or LED screens, speakers, or LEDs arranged to provide a user of the system with instructions regarding adjustments to be made to the fluid flow of the system.

The thermoelectric module 208 may be incorporated into the housing 202 in proximity to the reactor 210. The thermoelectric module 208 uses heat generated by the reactor 210 to generate the electrical energy needed to power the controller 206 and other electronic components of the housing 202 or the warming system 200. In other implementations, conventional battery systems can be used to power various components of the housing 202.

The reactor 210 is configured to fit within the opening 204 of the housing 202. The reactor 210 uses an exothermic chemical reaction to transmit heat into fluids flowing through the reactor 210. The reactor 210 may incorporate a number of frangible bladders or compartments that contain the reactants of a heating-generation chemical reaction, as described above. To begin fluid warming, the reactor 210 is flexed or otherwise manipulated, causing the frangible bladders or compartments to be breached, allowing the reactants to mix. The reactants then undergo a heat-generating reaction and the reactor 210 is slid into the opening 204 of the housing 202. A channel 212 is formed through the reactor 210. The channel 212 may include a length of tubing disposed within the reactor 210, or could include a non-frangible bladder or compartment. The channel 212 may include a number of turns to increase the length of the channel 212 within the reactor 210. By flowing a fluid through the channel 212, heat energy created by the chemical reaction occurring within the reactor 210 is communicated into the fluid for eventual delivery.

The couplings 214 and 216 allow for intravenous (or other) tubing to be connected to the channel 212 and may include, for example, a Luer-Lock or any other fastener configured to couple or affix an intravenous tube or other conduit or lumen to the channel 212.

To use the warming system 200, a new reactor 210 is first flexed or otherwise manipulated to initialize the warming chemical reaction. The reactor 210 is then placed within the opening 204 of the housing 202 and the housing 202 is powered-up (either by the delivery of heat energy to the thermoelectric module 208 or via an internal battery). A fluid delivery system (for example, an intravenous fluid bag, possibly via a infusion pump or rapid infuser) is connected to the coupling 216. Then another length of tubing is connected to the coupling 214. Fluid can then be flowed from the fluid delivery system, through the coupling 216 into the reactor 210 where it is warmed. From there, the warmed fluid flows out of the coupling 214 and into the attached tubing. When used to deliver warmed intravenous fluids to a patient, after the intravenous line is primed with warmed fluid, the distal end of the intravenous line connected to the coupling 214 is connected to the patient for delivery of the warmed fluid. After the appropriate amount of warmed fluid has been delivered to the patient, the intravenous line is removed from the patient and the reactor 210 (including the component attached to the couplings 214 and 216) can be disposed of. Because the intravenous fluid does not flow though or contact housing 202, the housing 202 can be reused with new the reactors 210 to deliver warmed fluid to other patients (or to deliver additional fluid to the first patient).

Figure 3:
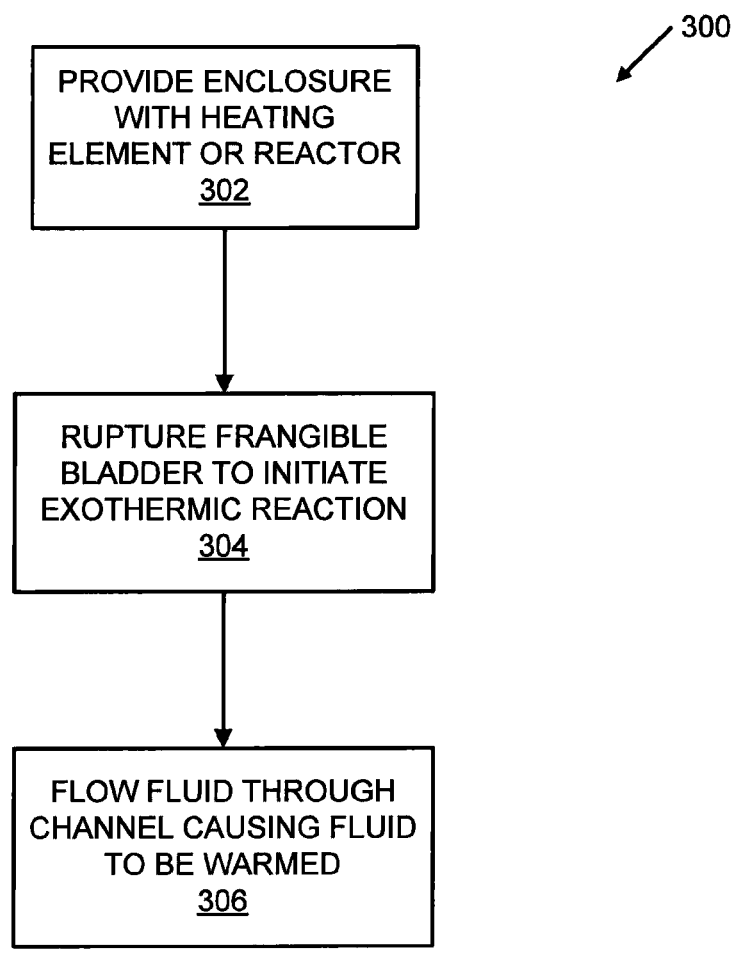
FIG. 3 is a flowchart illustrating a method for warming fluid in accordance with the present disclosure.

Referring now to FIG. 3, a flowchart illustrating a method for warming fluid 300 in accordance with the present disclosure is provided. In a first step 302, an enclosure containing a heating element or reactor is provided. The heating element may comprise a frangible bladder disposed at least partially within the enclosure, and a reactant of an exothermic reaction disposed within the frangible bladder. A channel may be formed through the enclosure so that the channel is at least partially enclosed by the enclosure. In step 304, the frangible bladder is ruptured or otherwise breached to initiate the exothermic reaction and cause the warming system to begin generating heat. In step 306, after rupturing the frangible bladder, a fluid is flowed through the channel of the enclosure to cause the fluid to be warmed by the exothermic reaction. In some cases, the method includes connecting a length of intravenous tubing to the channel to allow, for example, the warmed fluid to be delivered to a patient. This may occur, for example, in the delivery of intravenous fluids to a trauma victim.

In some cases, the method may include using a thermal sensor to detect a temperature of at least one of the enclosure and a portion of the channel. The thermal sensor may include an electronic device that is coupled to a component of the warming system. Alternatively, the sensor could include a temperature-sensitive color-changing film mounted to the enclosure, or another component of the system.

Using the thermal sensor, the flow rate of fluid through the warming system can be controlled. If the fluid is too cool, for example, the flow rate can be decreased allowing more heat to enter the fluid as it passes through the warming system. Conversely, if the fluid is too hot, the flow rate can be increased.

In one implementation of the present system, the heating element of the warming system generates heat using an exothermic reaction brought about by the mixing of magnesium and water according to the following reaction:

$$Mg(s) + 2\ H_2O \rightarrow Mg(OH)_2(s) + H_2(g) \quad (1)$$

The reaction shown in equation (1) generates a relatively high heat of reaction (e.g., $\Delta H_R = 352.96$ kJ/mol). The speed of the reaction can be increased by using powdered magnesium milled with small (~5-8 mol %) amounts of powdered iron in the presence of chloride anions catalyst. Powered Mg containing iron can be easily purchased while chloride anions can be introduced through a sodium chloride (NaCl) solution. Reaction rate experiments suggest a reaction rate constant, k, given by the expression $$k = k_o + \frac{k_c K[Cl^-]}{1 + K[Cl^-]}$$

where $K_c$ and $K_o$ are the rate constants with and without chloride ions.

The formation of dihydrogen $H_2(g)$ from the reaction can be a safety concern in oxygen-rich environments. In some cases, the formation of $H_2(g)$ can be minimized or suppressed. For example, the yield of dihydrogen from the reaction can be reduced by scavenging for the precursors of dihydrogen, namely solvated electrons and hydrogen radicals. Copper(II) has relatively high reactivity towards solvated electrons and hydrogen radicals, and could be used to suppress dihydrogen formation.

Depending on the reaction conditions, a secondary reaction consisting of the formation of $C_u^0$ takes place as a result of the presence of $C_uC_{12}$. This reaction increases the overall heat generated by approximately 70% and is given by the following reaction stoichiometry: $Mg + CuCl \rightarrow Mg^{2+} + Cu + 2Cl^-$.

In an alternative implementation, the exothermic reaction used to generate heat in the present system is based on an air- or oxygen-activated oxidation reaction. One such reaction can be generated through mixing of cellulose, iron, water, activated carbon, vermiculite, and salt. This mixture can generate heat when the iron is exposed to air and oxidized via the following reaction:

$$2\ Fe + 3/2\ O_2 + H_2O \rightarrow 2\ FeO(OH) \rightarrow Fe_2O_3 + H_2O \qquad (2)$$

The reaction shown in equation (2) does not producing hydrogen gas. The reaction is relatively stable and controllable, and certain ones of the nonreactive components may be provided in various quantities and ratios, e.g., to control the rate of reaction. Because iron is generally the limiting reactant in the reaction shown in equation (2), titration of the heat of reaction can be achieved by adding more iron.

When many substances undergo a spontaneous phase change they can also release energy associated with the phase change in the form of heat. For example, solidification or crystallization of a liquid is often accompanied by latent heat that is released. Certain substances can be provided in a stable metastable state (e.g., a supercooled liquid) and subsequently release heat when an exothermic solidification or crystallization reaction occurs.

The exemplary exothermic reactions shown in equations (1) and (2) above, or an appropriate phase-change reaction, can be used to provide a battery-less heat source. These reactions use reactants that may be readily available and inexpensive, and which have an established safety profile.

In order to design the exothermic reaction, it can be useful to model heat transfer from the reaction, through the present fluid delivery system to the patient. This allows for good control over the amount of heat that is delivered to the fluid and, consequently, the temperature of the fluid when the fluid reaches a patient. As discussed above, in one example a desired temperature for the fluid falls within the range of 37 to 41 degrees Celsius.

Accordingly, a heat transfer model for this reaction considers heat transfer due to both the chemical reaction occurring within the heater and convective heat transfer from the heater into the fluid.

The heat transfer modeling of the reaction can be performed in two distinct steps. First, a simplified one dimensional lumped model is developed to estimate the sizing of the chemical reactor (e.g., number moles of reactants, volume of reactor) and the dimensions of intravenous fluid delivery system. Next, a detailed 3D Finite Element Analysis (FEA) study is performed and used as a design tool.

The lumped model solves a 1D convective heat transfer problem for laminar flow in a tube under uniform heat flux boundary condition. The applied heat flux boundary condition is related to the heat of reaction, $\Delta H_R$, by the following equation:

$$\frac{dQ}{dt} = \dot{Q}(T) = -\Delta H_R N_{Mg0} \frac{dX}{dt}.$$

Considering a 1st order (in Magnesium) reaction rate law with an approximate estimate of the effects of reaction temperature, the reaction rate law can be written as:

$$r_{Mg}(T) = \left(k_o + \frac{k_c K[Cl^-]}{1 + K[Cl^-]}\right) e^{\frac{E}{R}\left(\frac{1}{T_a} - \frac{1}{T}\right)} [Mg]^1 \qquad (3)$$

-continued $$\frac{dX}{dt} = -\left(k_o + \frac{k_c K[Cl^-]}{1 + K[Cl^-]}\right) e^{\frac{E}{R}\left(\frac{1}{T_a} - \frac{1}{T}\right)} \qquad (4)$$

Therefore, as described above, the present system provides a lightweight battery-less heater configured to generate warming by conduction via an exothermic chemical reaction. Fluid is flowed in proximity to a heater that generates heat using an exothermic chemical reaction. By flowing fluid near the heater, heat energy is transferred from the heater into the fluid, thereby heating the fluid to a desired temperature. Once heated, for example in the case of intravenous fluid, the heated fluid can be delivered to a patient.

The chemical components of the reaction are disposed within the heater. When heating is initiated, the components mix and undergo an exothermic reaction. Tubing, such as intravenous tubing, is connected to, or inserted through, one or more channels running through the heater. As such, fluid flowing through the tubing and/or the channels is heated by the heater.

The chemical components of the exothermic reaction are separated from one another until warming is required by a frangible barrier. To initiate the exothermic reaction, the frangible barrier is broken or ruptured allowing for mixing of the components. Upon mixing, the system begins its heating process causing intravenous fluid located near the heater containing the chemical reaction to be warmed.

In one implementation, heat-sensitive indicators are combined with the present system to provide an indication to the user of when heating is occurring. The present system, therefore, allows the intravenous heating system to be placed proximal to the patient to eliminate the need to warm an entire bag of fluid. This system is lightweight and could become a standard part of every medic's aid bag in the deployed environment and would be beneficial to any austere casualty situation, for example, where fluid resuscitation is indicated.

In various implementations, the present system may be configured to deliver intravenous fluid with a target temperature between 37 and 41 degrees Celsius. Any appropriate fluid flow rate can be selected, but in one implementation the flow rate is between 50 and 100 cubic centimeters per minute (ccm).

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not specifically listed above. Accordingly, it is felt therefore that the scope of protection provided by this patent should not be viewed as limited by the above description, but rather should only be limited by the scope of the below claims.

What is claimed is:

1. An apparatus for warming a fluid for intravenous administration, comprising:
   an enclosure;
   a frangible bladder disposed at least partially within the enclosure;
   a first reactant of an exothermic reaction disposed within the frangible bladder;

a second reactant of the exothermic reaction disposed within the enclosure and external to the frangible bladder;

a channel at least partially enclosed by the enclosure, wherein the frangible bladder is configured to be ruptured to mix at least a portion of the first reactant and the second reactant to initiate the exothermic reaction, thereby warming at least a portion of the channel;

an input configured to receive a fluid from a fluid source and deliver the fluid to the channel to be exposed to the at least a portion of the channel warmed by the exothermic reaction; and an output configured to receive the fluid from the channel after being exposed to the at least a portion of the channel warmed by the exothermic reaction and to be coupled to an intravenous administration system to deliver the fluid for intravenous administration.

2. The apparatus of claim 1, further comprising a connector coupled to the output to couple the output to an intravenous administration tube.

3. The apparatus of claim 1, further comprising a thermal sensor connected to at least one of the enclosure and the channel and being configured to detect a temperature of at least one of the enclosure and a portion of the channel.

4. The apparatus of claim 3, wherein the thermal sensor comprises a temperature-sensitive color-changing film.

5. The apparatus of claim 1, wherein at least one of the first and second reactants comprises magnesium.

6. The apparatus of claim 1, wherein at least one of the first and second reactants comprises iron.

7. The apparatus of claim 1, wherein at least one of the first and second reactants comprises a phase-change material.

8. An apparatus for warming a fluid, comprising:
a housing having an opening;
a reactor sized to fit within the opening of the housing, the reactor including:
a frangible bladder configured to contain a first reactant of an exothermic reaction, and
a channel at least partially enclosed by the reactor, wherein the frangible bladder is configured to be ruptured to initiate the exothermic reaction, thereby warming at least a portion of the channel.

9. The apparatus of claim 8, further comprising a connector coupled to the channel, the connector being configured to couple to an intravenous tube.

10. The apparatus of claim 8, further comprising:
a thermal sensor connected to at least one of the reactor and the channel and being configured to detect a temperature of at least one of the reactor and a portion of the channel; and
a controller disposed within the housing and connected to the thermal sensor, the controller being configured to receive an indication of a temperature of at least one of the reactor and a portion of the channel from the thermal sensor.

11. The apparatus of claim 10, wherein the controller is configured to control at least one of a fluid flow rate and a temperature of the exothermic reaction based at least partially on the temperature.

12. A method of warming a fluid, comprising:
providing an enclosure, the enclosure including:
a frangible bladder disposed at least partially within the enclosure,
a reactant of an exothermic reaction disposed within the frangible bladder, and
a channel at least partially enclosed by the enclosure;
rupturing the frangible bladder to initiate the exothermic reaction; and
after rupturing the frangible bladder, flowing a fluid through the channel to cause the fluid to be warmed by the exothermic reaction.

13. The method of claim 12, including connecting a length of intravenous tubing to the channel.

14. The method of claim 12, including using a thermal sensor connected to at least one of the enclosure and the channel to detect a temperature of at least one of the enclosure and a portion of the channel.

15. The method of claim 14, wherein the thermal sensor comprises a temperature-sensitive color-changing film.

16. The method of claim 12, including using a thermal sensor to control a flow-rate of the fluid through the channel.

17. The method of claim 12, wherein the reactant comprises magnesium.

18. The method of claim 12, wherein the reactant comprises iron.

19. The method of claim 12, wherein the reactant comprises a phase-change material.

20. An apparatus for warming a fluid, comprising:
an enclosure;
a frangible bladder disposed at least partially within the enclosure;
a first reactant of an exothermic reaction disposed within the frangible bladder;
a second reactant of the exothermic reaction disposed within the enclosure and external to the frangible bladder; and
a channel at least partially enclosed by the enclosure, wherein the frangible bladder is configured to be ruptured to mix at least a portion of the first reactant and the second reactant to initiate the exothermic reaction, thereby warming at least a portion of the channel.

* * * * *